US00PP11598P

United States Patent [19]

Olesen et al.

[11] Patent Number: Plant 11,598

[45] Date of Patent: Oct. 24, 2000

[54] COMPACT FLORIBUNDA ROSE PLANT NAMED 'POULJOEY'

[75] Inventors: L. Pernille Olesen; Mogens N. Olesen, both of Fredensborg, Denmark

[73] Assignee: Poulsen Roser APS, Fredensborg, Denmark

[21] Appl. No.: 09/177,980

[22] Filed: Oct. 22, 1998

[51] Int. Cl.[7] ..... A01N 5/00

[52] U.S. Cl. ..... Plt./143

[58] Field of Search ..... Plt./141, 142, 143, Plt./147, 146

[56] References Cited

U.S. PATENT DOCUMENTS

P.P. 5,770 7/1986 DeRuiter ..... Plt./122
P.P. 6,261 8/1988 Olesen et al. ..... Plt./118

*Primary Examiner*—Howard J. Locker

[57] ABSTRACT

A new compact floribunda rose plant which has abundant flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of compact floribunda rose plant which originated from a controlled crossing between an unnamed seedling and an unnamed seedling. The two parents were crossed and the resulting seeds were planted in a controlled environment. The new variety is named 'POULjoey'.

The new rose may be distinguished from its seed parent, an unnamed seedling, by the following combination of characteristics:

1. The unnamed seedling is a yellow patio rose and 'POULjoey' is a compact floribunda with Red and Orange-Red colored flowers.

2. The unnamed seedling has smaller flowers and lower growth than 'POULjoey'.

3. The unnamed seedling is an offspring of 'Ruimired', U.S. Plant Pat. No. 5,770 and Texas, U.S. Plant Pat. No. 6,261.

The new variety may be distinguished from its pollen parent, an unnamed seedling, created by the same inventors, by the following combination of characteristics:

1. The unnamed seedling is a warm yellow patio rose and 'POULjoey' is a compact floribunda with Red and Orange-Red colored flowers.

2. The flowers, growth, and size of the plant of the unnamed seedling is smaller than 'POULjoey'.

The objective of the hybridization of this rose variety was to create a new and distinct variety with unique qualities, such as:

1. Uniform and abundant flowers;

2. Vigorous and compact growth;

3. Year-round flowering under glasshouse conditions;

4. Suitability for production from softwood cuttings or by traditional budding;

5. Durable flowers and foliage which make a variety suitable for distribution in the floral and nursery industry.

This combination of qualities is not present in previously available commercial cultivars of this type and distinguish 'POULjoey' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULjoey' was selected by the inventors as a single plant from the progeny of the hybridization in June 1990.

Asexual reproduction of 'POULjoey' by cuttings was first done in their nursery in Fredensborg, Denmark in March 1991 and by traditional budding in their nursery in Fredensborg, Denmark in August 1991 by L. Pernille and Mogens N. Olesen. This initial and other subsequent propagations conducted in controlled environments have demonstrated that the characteristics of 'POULjoey' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULjoey'. Specifically illustrated in SHEET 1:

1. Stem showing branching and the attachment of leaves, buds, and peduncles;

2. Flower bud receptacle, partially opened bud, and open bloom;

3. Flower petals, detached;

4. Sepals and pedicel;

5. Flowering stem as well as a bare stem exhibiting thorns;

6. Leaves.

DETAILED DESCRIPTION OF THE VARIETY

The following is a description of 'POULjoey', as observed in its growth in our nursery in Fredensborg, Denmark, as in a field nursery in Jackson County, Ore. Color references are made using The Royal Horticultural Society (London, England) Colour Chart, 1995, except where common terms of color are used.

For a comparison, several physical characteristics of the rose variety 'POULdace', a rose variety from the same inventors described and illustrated in U.S. Plant patent application Ser. No. 09/165,408 dated Oct. 2, 1998 are compared to 'POULjoey' in Chart 1.

CHART 1

| | 'POULjoey' | 'POULdace' |
|---|---|---|
| Color, upper surface, open bloom | Blend of Orange Group 28C and Red Group 39B-C | Yellow Group 9B |
| Color, reverse petal surface, open bloom | Blend of Red Group 54B and Oragne-Red Group 34C | Yellow Group 9C |
| Color, flower bud ¼ open | Orange Red Group 34B-35A | Yellow Group 9A |
| Leaf size | 110 mm (1) × 70 mm (w) | 90 mm (1) × 60 mm (w) |

Parents: Unnamed seedling×unnamed seedling.
Classification:
*Botanical.*—*Rosa hybrida.*
*Commercial.*—Floribunda.

FLOWER AND FLOWER BUD

Blooming habit: Continuous.
Flower bud:
*Size.*—Upon opening, 20 mm–25 mm in length from base of receptacle to end of bud.
*Bud form.*—Pointed ovoid.
*Bud color.*—As sepals unfold, blend of Orange-Red Group 34A–35A. Orange-Red Group 34B–35A at ¼ opening.
*Sepals.*—Green Group 139C–137D. Moderate to strong foliaceous appendages on three of the five sepals. Surfaces of sepals slightly pubescent. Above average numbers of stipitate glands present on margins and outermost sides of sepals.
*Receptacle.*—Surface: Smooth. Glabrous. Shape: Broadly funnel-shaped. Size: Small. 3 mm (h)×6 mm (w). Color: Green Group 138B.
*Peduncle.*—Surface: Above average numbers of stipitate glands. Stipitate glands with intonations of Red Group 39B. Length: 30 mm–40 mm average length. Color: Green Group 138A–B, with intonations of Red Group 39A.
*Borne.*—Singly and in small clusters of about 3–5.
Flower bloom:
*Fragrance.*—Light floral-tea fragrance.
*Duration.*—As a pot plant, flowers last from 8 to 10 days. As a cut flower 6 to 8 days.
*Size.*—Medium to large for a 15 cm pot rose. Average flower diameter is 50–60 mm when open.
*Form.*—Shape of flower when viewed from the side: Upon opening, upper part: Convex. Upon opening, lower part: Convex. Open flower, upper part: Flattened convex. Open flower, lower part: Concave.
*Petalage.*—Very double. Average range: 55–65 under normal conditions with 5–10 petaloids.
Color:
*Upon opening, petals.*—Outermost petals: Upper Surface: A blend of Orange Group 28B and 28C and Red Group 39B. Reverse Side: A blend of Red Group 39A–B and Orange-Red Group 34B. Innermost petals: Upper Surface: A blend of Orange-Red Group 31B and 32B. Reverse Side: A blend of Red Group 39A–B and Orange-Red Group 34B.
*Upon opening, basal petal spots.*—Outermost petals: Outer Side: Yellow Group 4B. Outerside coloration limited to point of attachment. Inner Side: Larger area of coloration than outer side. Yellow Group 12A, gradually blending into the petal color. Innermost petals: Outer Side: Yellow Group 4B. Some petals with Yellow 12B midrib on outerside. Inner Side: Yellow Group 12B.
*After opening, petals.*—Petal margins lighter in color. Outermost petals: Upper Surface: A blend of Orange Group 28C and Red Group 39B–C. Reverse Side: A blend of Red Group 54B and Orange-Red Group 34C. Innermost petals: Upper Surface: A blend of Orange-Red Group 32B and Red Group 54B. Reverse Side: A blend of Orange-Red Group 35B and Red Group 54B.
*Upon opening, basal petal spots.*— Outermost petals: Outer Side: Yellow Group 5B. Inner Side: Yellow Group 9B. Innermost petals: Outer Side: Yellow Group 5A. Inner Side: Yellow Group 5A.
General tonality: On open flower, a blend of Orange-Red Group 31B and Red Group 39B. No change in the general tonality at the end of the third day. Afterwards, general tonality is a blend of Orange-Red Group 32D and Red Group 39C.
Petals:
*Petal reflex.*—Petals are reflexed. Outermost petals are double reflexed forming a point.
*Petal edge.*—With point in center of margin.
*Shape.*—Round to deltoid.
*Petaloids.*—Present. Quantity : 5–10.
*Thickness.*—Thick.
*Arrangement.*—Imbricated.
Reproductive organs:
*Pollen.*—Color: Yellow Group 13B–14B. Abundance: Average.
*Anthers.*—Size: Medium. Color: Yellow Group 13B–14B. Abundance: Above average abundance.
*Filaments.*—Color: Yellow Group 14B.
*Stigmas.*—Stigmas generally superior in location to anthers. Color: Greyed-Green Group 195C.
*Styles.*—Color: Green-White Group 157B. Other: Immediately below stigma, strong intonation of Red-Purple Group 57C. Styles with thin hairs.
*Hips.*—None observed.

PLANT

Plant growth: Vigorous and upright to bushy, with uniform branching. When grown as a 15 cm pot plant, the average height of the plant itself is 22 to 24 cm and the average width is 20 to 22 cm. When grown as an own root plant in the nursery, the average height of the plant itself is 65–75 cm and the average width is 55–65 cm.
Stems:
*Color.*—Young wood: Green Group 143C. Older wood: Yellow-Green Group 146C.
*Thorns.*—Incidence: Moderate. Size: Average length: 5 mm. Color: Young: Yellow-Green Group 145D with intonations of Red Group 39D. Older: Greyed-Orange Group 177B. Shape: Concave to linear.
*Surface.*—Young wood: Smooth. Older wood: Smooth.
Plant foliage: Normal number of leaflets on normal leaves in middle of the stem: 5 leaflets.
*Leaf size.*—Medium-large. 110 mm (1)×70 mm (w).
*Abundance.*—Above average.

*Color.*—Upper Leaf Surface: Green Group 137A. Lower Leaf Surface: Green Group 138B. Juvenile foliage: Green Group 137C. Anthocyanin intonation: Limited. Location: Leaf margins, leaflet blades, petioles and rachis. Color: Greyed-Red Group 180A.

Plant leaves and leaflets:

*Stipules.*—Present. Stipitate glands present on margins. Size: 15 mm–18 mm. Color: Green Group 137B.

*Petiole.*—Length: 25 mm–30 mm. Color: Green Group 138B. Underneath: Smooth. Margins: With stipitate glands. Margins with small hairs and stipitate glands.

*Rachis.*—Color: Green Group 138B with intonations of Greyed-Red Group 179A. Underneath: Generally smooth, a few small prickles. Margins: With stipitate glands. Margins with small hairs and stipitate glands.

*Leaflet.*—Edge: Serrated. Shape: Ovate to round.

*Other.*—Moderately glossy finish. Thick texture.

Disease resistance: Above average resistance to mildew, black spot, and Botrytis under normal growing conditions in Half Moon Bay, Calif. and Jackson County, Ore.

We claim:

1. A new and distinct variety of rose plant of the compact floribunda class, substantially as herein illustrated and described as a distinct and novel rose variety due to its abundant flowers, vigorous and compact growth, year round flowering under glasshouse conditions, suitability for production from softwood cuttings in pots, and by traditional budding, and durable flowers and foliage which make the variety suitable for distribution in the floral industry.

* * * * *

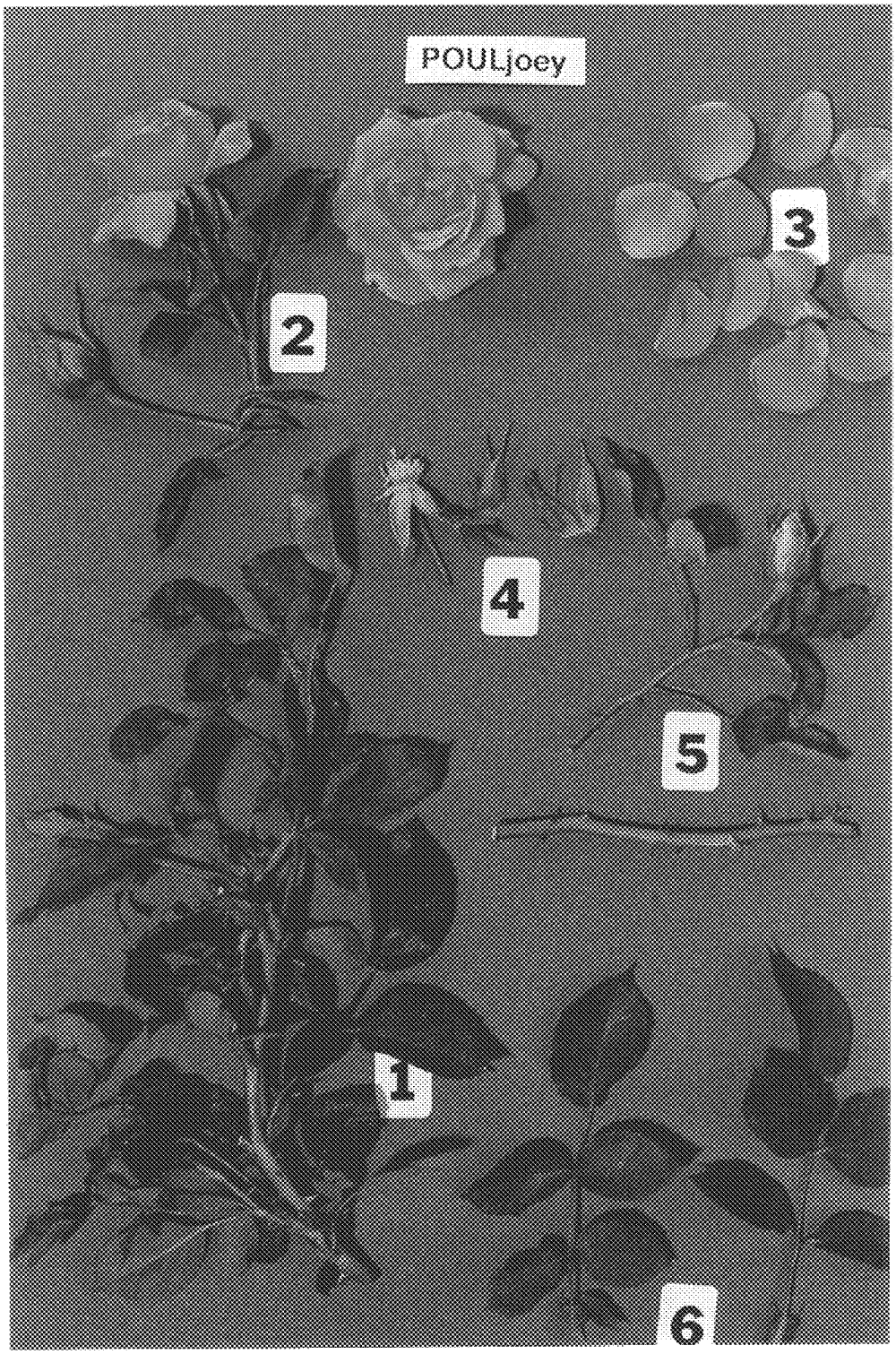
POULjoey
3
2
4
5
1
6